United States Patent
Glick et al.

(10) Patent No.: US 10,723,756 B2
(45) Date of Patent: Jul. 28, 2020

(54) CYCLIC DINUCLEOTIDES FOR TREATING CONDITIONS ASSOCIATED WITH STING ACTIVITY SUCH AS CANCER

(71) Applicant: Innate Tumor Immunity, Inc., Princeton, NJ (US)

(72) Inventors: Gary Glick, Ann Arbor, MI (US); Shomir Ghosh, Brookline, MA (US); Edward James Olhava, Newton, MA (US); William R. Roush, Jupiter, FL (US); Roger Jones, Martinsville, NJ (US)

(73) Assignee: Innate Tumor Immunity Inc., Princeton, NJ (US)

( * ) Notice: Subject to any disclaimer, the term of this patent is extended or adjusted under 35 U.S.C. 154(b) by 0 days.

(21) Appl. No.: 16/069,201

(22) PCT Filed: Jan. 11, 2017

(86) PCT No.: PCT/US2017/013049
§ 371 (c)(1),
(2) Date: Jul. 11, 2018

(87) PCT Pub. No.: WO2017/123657
PCT Pub. Date: Jul. 20, 2017

(65) Prior Publication Data
US 2019/0031708 A1    Jan. 31, 2019

Related U.S. Application Data

(60) Provisional application No. 62/436,795, filed on Dec. 20, 2016, provisional application No. 62/277,273, filed on Jan. 11, 2016.

(51) Int. Cl.
*A61K 31/7084* (2006.01)
*C07H 21/00* (2006.01)
(Continued)

(52) U.S. Cl.
CPC ......... *C07H 21/00* (2013.01); *A61K 31/7084* (2013.01); *A61K 39/3955* (2013.01); *A61K 45/06* (2013.01)

(58) Field of Classification Search
CPC ............ A61K 31/7084; A61K 39/3955; A61K 45/06; C07H 21/00
(Continued)

(56) References Cited

U.S. PATENT DOCUMENTS

2005/0203051 A1    9/2005  Karaolis et al.

OTHER PUBLICATIONS

Walz et al. Biochemistry (1976), 15(13), 2837-42. (Year: 1976).*
(Continued)

*Primary Examiner* — Kahsay Habte
(74) *Attorney, Agent, or Firm* — Elliott Korsen

(57) ABSTRACT

This disclosure features chemical entities (e.g., a compound that modulates (e.g., agonizes) Stimulator of Interferon Genes (STING), or a pharmaceutically acceptable salt, and/or hydrate, and/or cocrystal, and/or drug combination of the compound) that are useful, e.g., for treating a condition, disease or disorder in which a decrease or increase in STING activity (e.g., a decrease, e.g., a condition, disease or disorder associated with repressed or impaired STING signaling) contributes to the pathology and/or symptoms and/or progression of the condition, disease or disorder (e.g., cancer) in a subject (e.g., a human). This disclosure also features compositions as well as other methods of using and making the same.

2 Claims, No Drawings

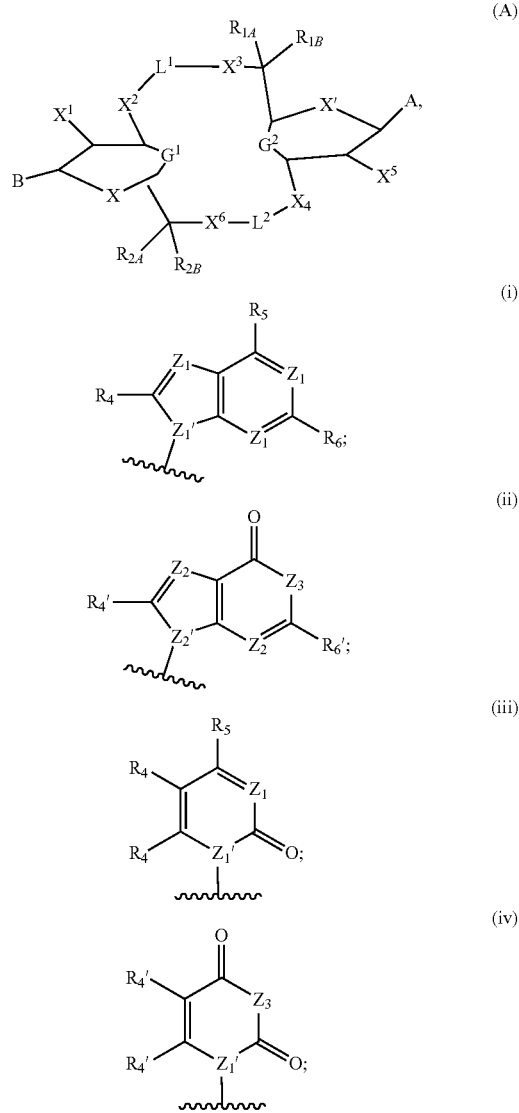

(51) Int. Cl.
*A61K 39/395* (2006.01)
*A61K 45/06* (2006.01)

(58) Field of Classification Search
USPC .......................................................... 544/272
See application file for complete search history.

(56) References Cited

OTHER PUBLICATIONS

Grajkowski, Andrzej, et al., "Convenient Synthesis of a Propargylated Cyclic (3'-5') Diguanylic Acid and Its "Click" Conjugation to a Biotinylated Azide", Bioconjugate Chemistry, 2010, vol. 21, pp. 2147-2152.

Luo, Yiling, et al., "Differential binding of 2'-bitinylated analog of c-di-GMP with c-di-GMP riboswitches and binding proteins", Molecular BioSystems, 2012, vol. 8, pp. 772-778.

Smietna, Michael, et al., "Solid-Phase Sysnthesis and Screeing of Macrocyclic Nucleotide-Hybrid Compounds Targeted to Hepatitis C NS5B", Chemistry—A European Journal, 2004, vol. 10, pp. 173-181.

U.S. Appl. No. 15/748,685, filed Jan. 30, 2018, Pending.

\* cited by examiner

CYCLIC DINUCLEOTIDES FOR TREATING CONDITIONS ASSOCIATED WITH STING ACTIVITY SUCH AS CANCER

CROSS REFERENCE TO RELATED APPLICATIONS

This application claims the benefit of U.S. Provisional Application No. 62/277,273, filed on Jan. 11, 2016 and U.S. Provisional Application No. 62/436,795, filed on Dec. 20, 2016, each of which is incorporated herein by reference in its entirety.

TECHNICAL FIELD

This disclosure features chemical entities (e.g., a compound that modulates (e.g., agonizes) Stimulator of Interferon Genes (STING), or a pharmaceutically acceptable salt, and/or hydrate, and/or cocrystal, and/or drug combination of the compound) that are useful, e.g., for treating a condition, disease or disorder in which a decrease or increase in STING activity (e.g., a decrease, e.g., a condition, disease or disorder associated with repressed or impaired STING signaling) contributes to the pathology and/or symptoms and/or progression of the condition, disease or disorder (e.g., cancer) in a subject (e.g., a human). This disclosure also features compositions as well as other methods of using and making the same.

BACKGROUND

STING, also known as transmembrane protein 173 (TMEM173) and MPYS/MITA/ERIS, is a protein that in humans is encoded by the TMEM173 gene. STING has been shown to play a role in innate immunity. STING induces type I interferon production when cells are infected with intracellular pathogens, such as viruses, mycobacteria and intracellular parasites. Type I interferon, mediated by STING, protects infected cells and nearby cells from local infection in an autocrine and paracrine manner. The STING pathway is a pathway that is involved in the detection of cytosolic DNA.

The STING signaling pathway is activated by cyclic dinucleotides (CDNs), which may be produced by bacteria or produced by antigen presenting cells in response to sensing cytosolic DNA. Unmodified CDNs have been shown to induce type I interferon and other co-regulated genes, which in turn facilitate the development of a specific immune response (see, e.g., Wu and Sun, et al., *Science* 2013, 339, 826-830). WO 2015/077354 discloses the use of STING agonists for the treatment of cancer.

SUMMARY

This disclosure features chemical entities (e.g., a compound that modulates (e.g., agonizes) Stimulator of Interferon Genes (STING), or a pharmaceutically acceptable salt, and/or hydrate, and/or cocrystal, and/or drug combination of the compound) that are useful, e.g., for treating a condition, disease or disorder in which a decrease or increase in STING activity (e.g., a decrease, e.g., a condition, disease or disorder associated with repressed or impaired STING signaling) contributes to the pathology and/or symptoms and/or progression of the condition, disease or disorder (e.g., cancer) in a subject (e.g., a human). In certain embodiments, the chemical entities described herein induce an immune response in a subject (e.g., a human). In certain embodiments, the chemical entities described herein induce STING-dependent type I interferon production in a subject (e.g., a human). This disclosure also features compositions as well as other methods of using and making the same.

An "agonist" of STING includes compounds that, at the protein level, directly bind or modify STING such that an activity of STING is increased, e.g., by activation, stabilization, altered distribution, or otherwise.

Certain compounds described herein that agonize STING to a lesser extent than a STING full agonist can function in assays as antagonists as well as agonists. These compounds antagonize activation of STING by a STING full agonist because they prevent the full effect of STING interaction. However, the compounds also, on their own, activate some STING activity, typically less than a corresponding amount of the STING full agonist. Such compounds may be referred to as "partial agonists of STING".

In some embodiments, the compounds described herein are agonists (e.g. full agonists) of STING. In other embodiments, the compounds described herein are partial agonists of STING.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

While not wishing to be bound by theory, it is believed that the partial agonists of STING described herein provide advantages with regard to treating the disorders described herein. By way of example, the partial agonists of STING described herein exhibit intrinsic activities that are expected to be both (i) high enough to induce an anti-tumor response (i.e., kill one or more tumor cells) and (ii) low enough to reduce the likelihood of producing toxicity-related side effects. As discussed above, partial agonists can antagonize activation of STING by a STING full agonist because they prevent the full effect of STING interaction, thereby reducing the activity of the STING full agonist. It is believed that this antagonism can also modulate (e.g., reduce) the toxicity profile of the STING full agonist. Accordingly, this disclosure contemplates methods in which the partial agonists of STING described herein are combined with one (or more) full agonists of STING (e.g., as described anywhere herein) to provide therapeutic drug combinations that are both efficacious and exhibit relatively low toxicity.

In one aspect, compounds of Formula A, or a pharmaceutically acceptable salt thereof, are featured:

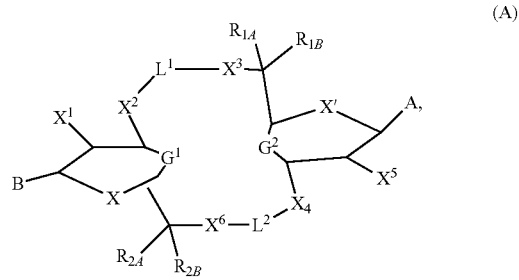

(A)

in which A, B, X, X', $G^1$, $G^2$, $X^1$, $X^2$, $X^3$, $X^4$, $X^5$, $X^6$, $L^1$, $L^2$, $R_{1A}$, $R_{1B}$, $R_{2A}$, and $R_{2B}$ can be as defined anywhere herein. $X^1$ and $X^5$ can each be independently "up" or "down."

In another aspect, compounds of Formula B, or a pharmaceutically acceptable salt thereof, are featured:

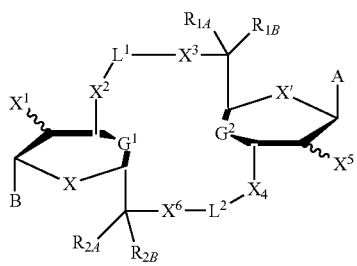

(B)

in which A, B, X, X', $G^1$, $G^2$, $X^1$, $X^2$, $X^3$, $X^4$, $X^5$, $X^6$, $L^1$, $L^2$, $R_{1A}$, $R_{1B}$, $R_{2A}$, and $R_{2B}$ can be as defined anywhere herein. $X^1$ and $X^5$ can each be independently "up" or "down."

In one aspect, compounds of Formula I, or a pharmaceutically acceptable salt thereof, are featured:

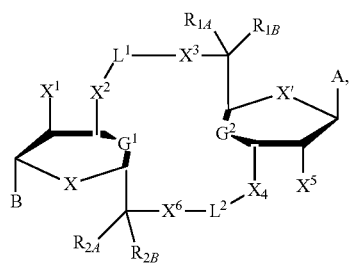

(I)

in which A, B, X, X', $G^1$, $G^2$, $X^1$, $X^2$, $X^3$, $X^4$, $X^5$, $X^6$, $L^1$, $L^2$, $R_{1A}$, $R_{1B}$, $R_{2A}$, and $R_{2B}$ can be as defined anywhere herein.

In one aspect, compounds of Formula A', or a pharmaceutically acceptable salt thereof, are featured:

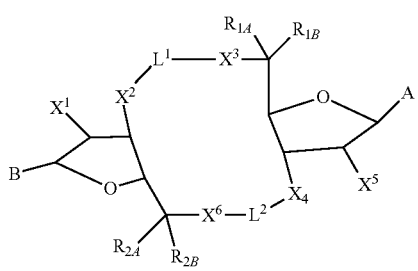

(A')

in which A, B, X, X', $X^1$, $X^2$, $X^3$, $X^4$, $X^5$, $X^6$, $L^1$, $L^2$, $R_{1A}$, $R_{1B}$, $R_{2A}$, and $R_{2B}$ can be as defined anywhere herein. $X^1$ and $X^5$ can each be independently "up" or "down."

In another aspect, compounds of Formula B', or a pharmaceutically acceptable salt thereof, are featured:

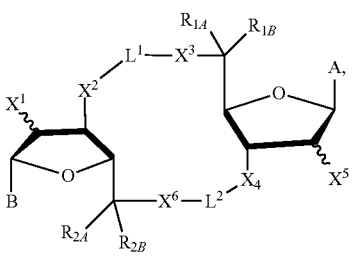

(B')

in which A, B, X, X', $X^1$, $X^2$, $X^3$, $X^4$, $X^5$, $X^6$, $L^1$, $L^2$, $R_{1A}$, $R_{1B}$, $R_{2A}$, and $R_{2B}$ can be as defined anywhere herein. $X^1$ and $X^5$ can each be independently "up" or "down."

In another aspect, compounds of Formula I-A, or a pharmaceutically acceptable salt thereof, are featured:

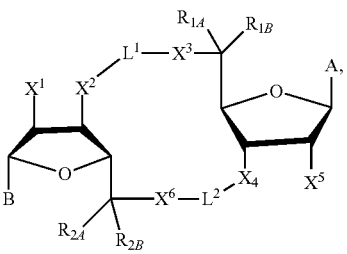

(I-A)

in which A, B, X, X', $X^1$, $X^2$, $X^3$, $X^4$, $X^5$, $X^6$, $L^1$, $L^2$, $R_{1A}$, $R_{1B}$, $R_{2A}$, and $R_{2B}$ can be as defined anywhere herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing) STING activity are featured that include contacting STING with a chemical entity described herein (e.g., a compound described generically or specifically herein or a pharmaceutically acceptable salt thereof or compositions containing the same). Methods include in vitro methods, e.g., contacting a sample that includes one or more cells comprising STING (e.g., innate immune cells, e.g., mast cells, macrophages, dendritic cells (DCs), and natural killer cells) with the chemical entity. The contacting can, in some cases, induce an immune response sufficient to kill at least one of the one or more cancer cells. Methods can also include in vivo methods; e.g., administering the chemical entity to a subject (e.g., a human) having a disease in which repressed or impaired STING signaling contributes to the pathology and/or symptoms and/or progression of the disease (e.g., cancer; e.g., a refractory cancer).

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same).

In a further aspect, methods of inducing an immune response (e.g., an innate immune response) in a subject in need thereof are featured that include administering to the subject an effective amount of a chemical entity described herein (e.g., a compound described generically or specifically herein or a pharmaceutically acceptable salt thereof or compositions containing the same).

In another aspect, methods of inducing induce STING-dependent type I interferon production in a subject in need thereof are featured that include administering to the subject an effective amount of a chemical entity described herein (e.g., a compound described generically or specifically herein or a pharmaceutically acceptable salt thereof or compositions containing the same).

In a further aspect, methods of treatment of a disease in which repressed or impaired STING signaling contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering to a subject having a disease in which repressed or impaired STING signaling contributes to the pathology and/or symptoms and/or progression of the disease an effective amount of a chemical entity described herein (e.g., a compound described generically or specifically herein or a pharmaceutically acceptable salt thereof or compositions containing the same).

In a further aspect, methods of treatment that include administering to a subject a chemical entity described herein (e.g., a compound described generically or specifically herein or a pharmaceutically acceptable salt thereof or compositions containing the same), wherein the chemical entity is administered in an amount effective to treat a disease in which repressed or impaired STING signaling contributes to the pathology and/or symptoms and/or progression of the disease, thereby treating the disease.

Embodiments can include one or more of the following features.

The chemical entity can be administered in combination with one or more additional cancer therapies (e.g., surgery, radiotherapy, chemotherapy, toxin therapy, immunotherapy, cryotherapy or gene therapy, or a combination thereof; e.g., chemotherapy that includes administering one or more (e.g., two, three, four, five, six, or more) additional chemotherapeutic agents. Non-limiting examples of additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a vinca alkaloid and/or a taxane; e.g., Vincristine, Vinblastine, Vinorelbine and/or Vindesine Taxol, Pacllitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM$_3$, lymphocyte activation gene 3 protein (LAG3), MHC class II-LAG3, 4-IBB-4-IBB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, LIGHT, HVEM-BTLA-CD160, CD80, CD80-PDL-1, PDL2-CD80, CD244, CD48-CD244, CD244, ICOS, ICOS-ICOS ligand, B7-H$_3$, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM$_3$, SIRPA-CD47, VEGF, Neuropilin, CD160, CD30, and CD155 (e.g., CTLA-4 or PD1 or PD-L1).

The subject can have cancer; e.g., the subject has undergone and/or is undergoing and/or will undergo one or more cancer therapies.

Non-limiting examples of cancer include melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma. In certain embodiments, the cancer can be a refractory cancer.

The chemical entity can be administered intratumorally.
The methods can further include identifying the subject.
Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification are incorporated herein by reference in their entireties.

As used herein, the term "STING" is meant to include, without limitation, nucleic acids, polynucleotides, oligonucleotides, sense and antisense polynucleotide strands, complementary sequences, peptides, polypeptides, proteins, homologous and/or orthologous STING molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21*st ed.*; Lippincott Williams & Wilkins: Philadelphia, Pa., 2005; *Handbook of Pharmaceutical Excipients*, 6*th* ed.; Rowe et al., Eds.; The Pharmaceutical Press and the American Pharmaceutical Association: 2009; *Handbook of Pharmaceutical Additives*, 3*rd ed.*; Ash and Ash Eds.; Gower Publishing Company: 2007; *Pharmaceutical Preformulation and Formulation*, 2*nd ed.*; Gibson Ed.; CRC Press LLC: Boca Raton, Fla., 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "alkylene" refers to a divalent alkyl (e.g., —CH$_2$—).

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent. Examples of aryl groups include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the accompanying drawings and the description below. Other features and advantages of the invention will be apparent from the description and drawings, and from the claims.

DETAILED DESCRIPTION

This disclosure features chemical entities (e.g., a compound that modulates (e.g., agonizes) Stimulator of Interferon Genes (STING), or a pharmaceutically acceptable salt, and/or hydrate, and/or cocrystal, and/or drug combination of the compound) that are useful, e.g., for treating a condition, disease or disorder in which a decrease or increase in STING activity (e.g., a decrease, e.g., a condition, disease or disorder associated with repressed or impaired STING signaling) contributes to the pathology and/or symptoms and/or progression of the condition, disease or disorder (e.g., cancer) in a subject (e.g., a human). In certain embodiments, the chemical entities described herein induce an immune response in a subject (e.g., a human). In certain embodiments, the chemical entities described herein induce STING-dependent type I interferon production in a subject (e.g., a human). This disclosure also features compositions as well as other methods of using and making the same.

Formula I Compounds

In one aspect, compounds of Formula A, or a pharmaceutically acceptable salt thereof,

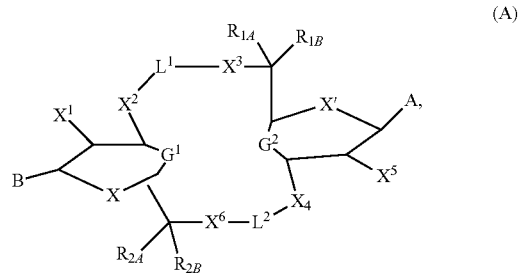

wherein:
A and B are each independently selected from the group consisting of Formulae (i), (ii), (iii), and (iv):

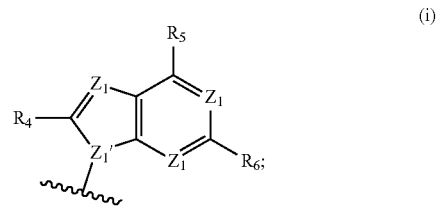

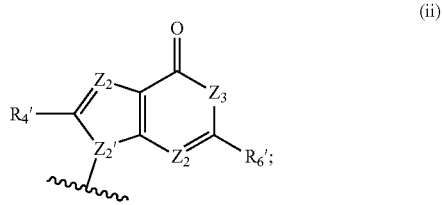

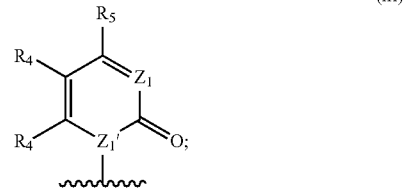

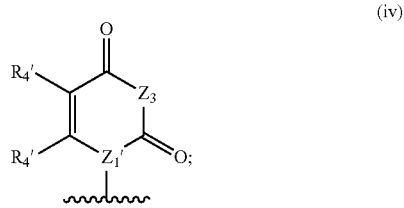

X and X' are each independently selected from the group consisting of O, S, S(O), SO$_2$, CH$_2$, CHF, CF$_2$, CH$_2$O, OCH$_2$, CH$_2$CH$_2$, CH═CH, NR$^3$, and N(O$^-$)R$^3$;

G$^1$ is a bond connecting (i) the carbon directly attached to X$^2$ and (ii) the carbon directly attached to C(R$^{2A}$)(R$^{2B}$)(X$^6$), or is C(R$^{G1A}$)(R$^{G1B}$);

G$^2$ is a bond connecting (i) the carbon directly attached to X$^4$ and (ii) the carbon directly attached to C(R$^{1A}$)(R$^{1B}$)(C$^3$); or is C(R$^{G2A}$)(R$^{G2B}$)(X$^3$); or is C(R$^{G2A}$)(R$^{G2B}$);

X$^1$ and X$^5$ are each independently selected from the group consisting of H, C$_{1-4}$ alkyl, C$_{1-4}$ haloalkyl, halo (e.g., F), —CN, —NO$_2$, —N$_3$, —OH, —OR$^{a1}$, —SH, —C(O)H, —C(O)R$^{a1}$, —C(O)NR$^{c1}$R$^{d1}$, —C(O)OH, —C(O)OR$^{a1}$, —OC(O)H, —OC(O)R$^{a1}$, —OC(O)NR$^{b1}$R$^{c1}$, —C(═NR$^{e1}$)NR$^{b1}$R$^{c1}$, —NR$^{d1}$C(═NR$^{e1}$)NR$^{b1}$R$^{c1}$, —NR$^{b1}$R$^{c1}$, —$^+$NR$^{b1}$R$^{c1}$R$^{d1}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, —NR$^{d1}$S(O)$_2$NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$;

X$^2$, X$^3$, X$^4$ and X$^6$ are each independently selected from the group consisting of O and S;

L$^1$ is

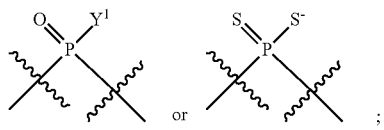

or ;

L$^2$ is

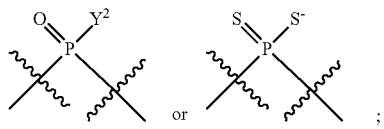

or ;

Y$^1$ and Y$^2$ are each independently selected from the group consisting of —OH, —OR$^{a1}$, O$^-$, —SH, —SR$^{a1}$, S$^-$; —NR$^{b1}$R$^{c1}$;

R$^{1A}$ and R$^{1B}$ are each independently selected from the group consisting of H; halo; C$_{1-4}$ alkyl; C$_{1-4}$ haloalkyl; C$_{2-4}$ alkenyl; C$_{2-4}$ alkynyl; and C$_{3-5}$ cycloalkyl, which is optionally substituted with from 1-4 independently selected C$_{1-4}$ alkyl; or R$^{1A}$ and R$^{1B}$, together with the carbon atom to which each is attached, form a C$_{3-5}$ cycloalkyl or heterocyclyl, including from 4-5 ring atoms, wherein from 1-2 (e.g., 1) ring atoms are independently selected from the group consisting of nitrogen and oxygen (e.g oxetane), wherein the C$_{3-5}$ cycloalkyl or heterocyclyl ring can each be optionally substituted with from 1-4 independently selected C$_{1-4}$ alkyl;

R$^{2A}$ and R$^{2B}$ are each independently selected from the group consisting of H; halo; C$_{1-4}$ alkyl; C$_{1-4}$ haloalkyl; C$_{2-4}$ alkenyl; C$_{2-4}$ alkynyl; and C$_{3-5}$ cycloalkyl, which is optionally substituted with from 1-4 independently selected C$_{1-4}$ alkyl; or R$^{2A}$ and R$^{2B}$, together with the carbon atom to which each is attached, form a C$_{3-5}$ cycloalkyl or heterocyclyl, including from 4-5 ring atoms, wherein from 1-2 (e.g., 1) ring atoms are independently selected from the group consisting of nitrogen and oxygen (e.g., oxetane), wherein the C$_{3-5}$ cycloalkyl or heterocyclyl ring can each be optionally substituted with from 1-4 independently selected C$_{1-4}$ alkyl, Z$_1$ is N or C—R$^4$;
Z$_{1'}$ is N or C—H;
Z$_2$ is N or C—R$^{4'}$;
Z$_{2'}$ is N or C—H;
Z$_3$ is N—R$^3$ or C—R$^4$;

each occurrence of R$^{a1}$ is independently selected from the group consisting of:

C$_{1-10}$ alkyl optionally substituted with from 1-3 R$^A$;
C$_{1-10}$ haloalkyl optionally substituted with from 1-3 R$^A$;
C$_{2-10}$ alkenyl optionally substituted with from 1-3 R$^B$;
C$_{2-10}$ alkynyl optionally substituted with from 1-3 R$^B$;
C$_{3-10}$ cycloalkyl optionally substituted with from 1-5 R$^C$;
(C$_{3-10}$ cycloalkyl)-C$_{1-6}$ alkylene, wherein the alkylene serves as the point of attachment, and wherein the C$_{3-10}$ cycloalkyl optionally substituted with from 1-5 R$^C$;
heterocyclyl, including from 3-10 ring atoms, wherein from 1-3 ring atoms are independently selected from the group consisting of nitrogen, oxygen and sulfur, and which is optionally substituted with from 1-5 R$^C$;
(heterocyclyl as defined above)-C$_{1-6}$ alkylene, wherein the alkylene serves as the point of attachment, and wherein the heterocyclyl is optionally substituted with from 1-5 R$^C$;
C$_{6-10}$ aryl optionally substituted with from 1-5 R$^D$;
heteroaryl including from 5-10 ring atoms, wherein from 1-4 ring atoms are independently selected from the group consisting of nitrogen, oxygen and sulfur, and which is optionally substituted with from 1-5 R$^D$; and
(heteroaryl as defined above)-C$_{1-6}$ alkylene, wherein the alkylene serves as the point of attachment, and wherein the heteroaryl optionally substituted with from 1-5 R$^D$;

each occurrence of R$^3$, R$^{b1}$, R$^{c1}$, R$^{d1}$, and R$^{e1}$ is independently selected from the group consisting of: H; R$^{a1}$; —C(O)H, —C(O)R$^{a1}$, —C(O)NR$^{c1}$R$^{d1}$, —C(O)OR$^{a1}$, —OC(O)H, —C(═NR$^{e1}$)NR$^{b1}$R$^{c1}$, —NR$^{d1}$C(═NR$^{e1}$)NR$^{b1}$R$^{c1}$, —NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$; or R$^{b1}$ and R$^{c1}$ taken together with the nitrogen atom to which each is attached form a heterocyclyl, including from 3-10 ring atoms, wherein from 1-3 ring atoms are independently selected from the group consisting of nitrogen, oxygen and sulfur, and which is optionally substituted with from 1-5 R$^C$; (e.g., azetidinyl, morpholino, piperidinyl);

each occurrence of R$^{G1A}$, R$^{G1B}$, R$^{G1A}$, R$^{G1B}$, R$^4$, R$^{4'}$, R$^5$, R$^{6'}$ is independently selected from the group consisting of: H; R$^{a1}$; halo, —CN, —NO$_2$, —N$_3$, —OH, —OR$^{a1}$, —SH, —SR$^{a1}$, —C(O)H, —C(O)R$^{a1}$, —C(O)NR$^{c1}$R$^{d1}$, —C(O)OH, —C(O)OR$^{a1}$, —OC(O)H, —OC(O)R$^{a1}$, —OC(O)NR$^{b1}$R$^{c1}$, —C(═NR$^{e1}$)NR$^{b1}$R$^{c1}$, —NR$^{d1}$C(═NR$^{e1}$)NR$^{b1}$R$^{c1}$, —NR$^{b1}$R$^{c1}$, —N$^+$R$^{b1}$R$^{c1}$R$^{d1}$, —NR$^{d1}$C(O)H, —NR$^{d1}$C(O)R$^{a1}$, —NR$^{c1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, —NR$^{d1}$S(O)$_2$NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$;

each occurrence of R$^A$ is independently selected from the group consisting of: —CN; —OH; C$_{1-6}$ alkoxy; C$_{1-6}$ haloalkoxy; —C(O)NRR', wherein R' and R" are each independently selected from H and C$_{1-4}$ alkyl; —C(O)OH; —C(O)O(C$_{1-6}$ alkyl); and —NR'R'", wherein R" and R'" are each independently selected from the group consisting of H, C$_{1-4}$ alkyl, —SO$_2$(C$_{1-6}$ alkyl), —C(O)(C$_{1-6}$ alkyl), and —C(O)O(C$_{1-6}$ alkyl);

each occurrence of R$^B$ is independently selected from the group consisting of: halo; —CN; —OH; C$_{1-6}$ alkoxy; C$_{1-6}$ haloalkoxy; —C(O)NRR', wherein R' and R" are each independently selected from H and C$_{1-4}$ alkyl; —C(O)OH; —C(O)O(C$_{1-6}$ alkyl); and —NR"R'", wherein R' and R'" are each independently selected from the group consisting of H, $C_{1-4}$ alkyl, —$SO_2(C_{1-6}$ alkyl), —$C(O)(C_{1-6}$ alkyl), and —$C(O)O(C_{1-6}$ alkyl);

each occurrence of $R^C$ is independently selected from the group consisting of: $C_{1-6}$ alkyl; $C_{1-4}$ haloalkyl; halo; —CN; —OH; oxo; $C_{1-6}$ alkoxy; $C_{1-6}$ haloalkoxy; —C(O)NR'R", wherein R' and R" are each independently selected from H and $C_{1-4}$ alkyl; —$C(O)(C_{1-6}$ alkyl); —C(O)OH; —C(O)O ($C_{1-6}$ alkyl); and —NR'R''', wherein R' and R''' are each independently selected from the group consisting of H, $C_{1-4}$ alkyl, —$SO_2(C_{1-6}$ alkyl), —$C(O)(C_{1-6}$ alkyl), and —C(O)O ($C_{1-6}$ alkyl);

each occurrence of $R^D$ is independently selected from the group consisting of:
- $C_{1-6}$ alkyl optionally substituted with from 1-2 substituents independently selected from the group consisting of: —OH, $C_{1-4}$ alkoxy; $C_{1-4}$ haloalkoxy; —$NH_2$, —NH ($C_{1-4}$ alkyl), and —N($C_{1-4}$ alkyl)$_2$;
- $C_{1-4}$ haloalkyl;
- $C_{2-4}$ alkenyl;
- $C_{2-4}$ alkynyl;
- halo;
- —CN;
- —$NO_2$;
- —$N_3$;
- —OH;
- $C_{1-6}$ alkoxy;
- $C_{1-6}$ haloalkoxy;
- —C(O)NRR', wherein R' and R" are each independently selected from H and $C_{1-4}$ alkyl;
- —$SO_2$NRR', wherein R' and R" are each independently selected from H and $C_{1-4}$ alkyl;
- —$C(O)(C_{1-6}$ alkyl);
- —C(O)OH;
- —C(O)O($C_{1-6}$ alkyl);
- —$SO_2(C_{1-6}$ alkyl),
- —NR"R''', wherein R" and R''' are each independently selected from the group consisting of H, $C_{1-4}$ alkyl, —$SO_2(C_{1-6}$ alkyl), —$C(O)(C_{1-6}$ alkyl), and —C(O)O ($C_{1-6}$ alkyl);
- ($C_{3-10}$ cycloalkyl)-($CH_2$)$_{0-2}$, wherein the $CH_2$ (when present) serves as the point of attachment, and wherein the $C_{3-10}$ cycloalkyl is optionally substituted with from 1-5 independently selected $C_{1-4}$ alkyl;
- (heterocyclyl as defined above)-($CH_2$)$_{0-2}$, wherein the $CH_2$ (when present) serves as the point of attachment, and wherein the heterocyclyl is optionally substituted with from 1-5 independently selected $C_{1-4}$ alkyl;
- (phenyl)-($CH_2$)$_{0-2}$, wherein the $CH_2$ (when present) serves as the point of attachment, and wherein the phenyl is optionally substituted with from 1-5 substituents independently selected from halo, $C_{1-4}$ alkyl, —$CF_3$, —$OCH_3$, —$SCH_3$, —$OCF_3$, —$NO_2$, —$N_3$, —$NH_2$, —NH($C_{1-4}$ alkyl), —N($C_{1-4}$ alkyl)$_2$, —C(O) ($C_{1-4}$ alkyl), —C(O)OH, —C(O)O($C_{1-4}$ alkyl), —$SO_2$ ($CH_3$), and cyclopropyl; and
- (heteroaryl as defined above)-($CH_2$)$_{0-2}$, wherein the $CH_2$ (when present) serves as the point of attachment, and wherein the phenyl is optionally substituted with from 1-5 substituents independently selected from halo, $C_{1-4}$ alkyl, —$CF_3$, —$OCH_3$, —$SCH_3$, —$OCF_3$, —$NO_2$, —$N_3$, —$NH_2$, —NH($C_{1-4}$ alkyl), —N($C_{1-4}$ alkyl)$_2$, —$C(O)(C_{1-4}$ alkyl), —C(O)OH, —C(O)O($C_{1-4}$ alkyl), —$SO_2(CH_3)$, and cyclopropyl.

In another aspect, of compounds having formula (A) can be as defined as follows:

A and B are each independently selected from the group consisting of Formulae (i), (ii), (iii), and (iv):

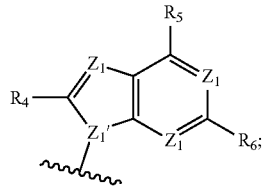

(i)

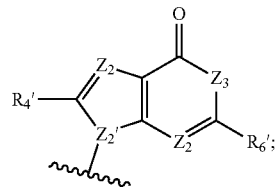

(ii)

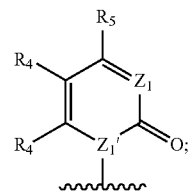

(iii)

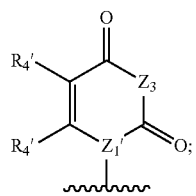

(iv)

X and X' are each independently selected from the group consisting of O, S, S(O), $SO_2$, $CH_2$, CHF, $CF_2$, $CH_2O$, $OCH_2$, $CH_2CH_2$, CH=CH, $NR^3$, and $N(O^-)^3$;

$G^1$ is a bond connecting (i) the carbon directly attached to $X^2$ and (ii) the carbon directly attached to $C(R^{2A})(R^{2B})(X^6)$, or is $C(R^{G1A})(R^{G1B})$;

$G^2$ is a bond connecting (i) the carbon directly attached to $X^4$ and (ii) the carbon directly attached to $C(R^{1A})(R^{1B})(X^3)$; or is $C(R^{G2A})(R^{G2B})$;

$X^1$ and $X^5$ are each independently selected from the group consisting of H, $C_{1-4}$ alkyl, $C_{1-4}$ haloalkyl, halo (e.g., F), —CN, —$NO_2$, —$N_3$, —OH, —$OR^{a1}$, —SH, —$SR^{a1}$, —C(O)H, —$C(O)R^{a1}$, —$C(O)NR^{b1}R^{c1}$, —C(O)OH, —$C(O)OR^{a1}$, —OC(O)H, —$OC(O)R^{a1}$, —$OC(O)NR^{b1}R^{c1}$, —$C(=NR^{e1})NR^{b1}R^{c1}$, —$NR^{d1}C(=NR^{e1})NR^{b1}R^{c1}$, —$NR^{b1}R^{c1}$, —$^+NR^{b2}R^{c2}R^{d2}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, —$NR^{d1}S(O)_2NR^{b1}R^{c1}$, —$S(O)R^{a1}$, —$S(O)NR^{b1}R^{c1}$, —$S(O)_2R^{a1}$, and —$S(O)_2NR^{b1}R^{c1}$;

$X^2$, $X^3$, $X^4$ and $X^6$ are each independently selected from the group consisting of O and S;

$L^1$ is

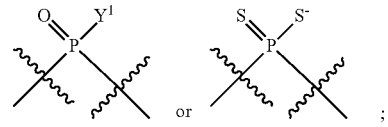

$L^2$ is

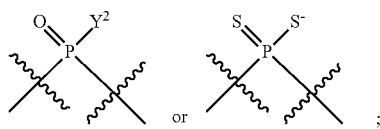

$Y^1$ and $Y^2$ are each independently selected from the group consisting of —OH, —OR$^{a1}$, O$^-$, —SH, —SR$^{a1}$, S$^-$; and —NR$^{b1}$R$^{c1}$;

R$^{1A}$ and R$^{1B}$ are each independently selected from the group consisting of H; halo; C$_{1-4}$ alkyl; C$_{1-4}$ haloalkyl; C$_{2-4}$ alkenyl; C$_{2-4}$ alkynyl; and C$_{3-5}$ cycloalkyl, which is optionally substituted with from 1-4 independently selected C$_{1-4}$ alkyl; or R$^{1A}$ and R$^{1B}$, together with the carbon atom to which each is attached, form a C$_{3-5}$ cycloalkyl or heterocyclyl, including from 4-5 ring atoms, wherein from 1-2 (e.g., 1) ring atoms are independently selected from the group consisting of nitrogen and oxygen (e.g. oxetane), wherein the C$_{3-5}$ cycloalkyl or heterocyclyl ring can each be optionally substituted with from 1-4 independently selected C$_{1-4}$ alkyl;

R$^{2A}$ and R$^{2B}$ are each independently selected from the group consisting of H; halo; C$_{1-4}$ alkyl; C$_{1-4}$ haloalkyl; C$_{2-4}$ alkenyl; C$_{2-4}$ alkynyl; and C$_{3-5}$ cycloalkyl, which is optionally substituted with from 1-4 independently selected C$_{1-4}$ alkyl; or R$^{2A}$ and R$^{2B}$, together with the carbon atom to which each is attached, form a C$_{3-5}$ cycloalkyl or heterocyclyl, including from 4-5 ring atoms, wherein from 1-2 (e.g., 1) ring atoms are independently selected from the group consisting of nitrogen and oxygen (e.g., oxetane), wherein the C$_{3-5}$ cycloalkyl or heterocyclyl ring can each be optionally substituted with from 1-4 independently selected C$_{1-4}$ alkyl, $Z_1$ is N or C—R$^4$;
$Z_{1'}$ is N or C—H;
$Z_2$ is N or C—R$^{4'}$;
$Z_{2'}$ is N or C—H;
$Z_3$ is N—R$^3$ or C—R$^4$;

each occurrence of R$^{a1}$ is independently selected from the group consisting of:
C$_{1-10}$ alkyl optionally substituted with from 1-3 R$^A$;
C$_{1-10}$ haloalkyl optionally substituted with from 1-3 R$^A$;
C$_{2-10}$ alkenyl optionally substituted with from 1-3 R$^B$,
C$_{2-10}$ alkynyl optionally substituted with from 1-3 R$^B$,
C$_{3-10}$ cycloalkyl optionally substituted with from 1-5 R$^C$;
(C$_{3-10}$ cycloalkyl)-C$_{1-6}$ alkylene, wherein the alkylene serves as the point of attachment, and wherein the C$_{3-10}$ cycloalkyl optionally substituted with from 1-5 R$^C$;
heterocyclyl, including from 3-10 ring atoms, wherein from 1-3 ring atoms are independently selected from the group consisting of nitrogen, oxygen and sulfur, and which is optionally substituted with from 1-5 R$^C$;
(heterocyclyl as defined above)-C$_{1-6}$ alkylene, wherein the alkylene serves as the point of attachment, and wherein the heterocyclyl is optionally substituted with from 1-5 R$^C$;
C$_{6-10}$ aryl optionally substituted with from 1-5 R$^D$;
heteroaryl including from 5-10 ring atoms, wherein from 1-4 ring atoms are independently selected from the group consisting of nitrogen, oxygen and sulfur, and which is optionally substituted with from 1-5 R$^D$; and
(heteroaryl as defined above)-C$_{1-6}$ alkylene, wherein the alkylene serves as the point of attachment, and wherein the heteroaryl optionally substituted with from 1-5 R$^D$;

each occurrence of R$^{b1}$ and R$^{c1}$ is independently selected from the group consisting of: H; R$^{a1}$; —C(O)H, —C(O)R$^{a1}$, —C(O)NR$^{b3}$R$^{c3}$; —C(O)OR$^{a1}$, —OC(O)H, —C(=NR$^{e2}$)NR$^{b3}$R$^{c3}$, —NR$^{23}$C(=NR$^{e2}$)NR$^{b3}$R$^{c3}$, —NR$^{b3}$R$^{c3}$, —S(O)R$^{a1}$, —S(O) NR$^{b3}$R$^{c3}$, —S(O)$_2$R$^{a1}$, and —S(O)$_2$NR$^{b3}$R$^{c3}$; or
R$^{b1}$ and R$^{c1}$ taken together with the nitrogen atom to which each is attached form a heterocyclyl, including from 3-10 ring atoms, wherein from 1-3 ring atoms are independently selected from the group consisting of nitrogen, oxygen and sulfur, and which is optionally substituted with from 1-5 R$^C$; (e.g., azetidinyl, morpholino, piperidinyl);

each occurrence of R$^3$, R$^{d1}$, and R$^{e1}$ is independently selected from the group consisting of: H; R$^{a1}$; —C(O)H, —C(O)R$^{a1}$, —C(O)NR$^{b3}$R$^{c3}$, —C(O)OR$^{a1}$, —OC(O)H, —C(=NR$^{e2}$)NR$^{b3}$R$^{c3}$, —NR$^{d3}$C(=NR$^{e2}$)NR$^{b3}$R$^{c3}$, —NR$^{b3}$R$^{c3}$, —S(O)R$^{a1}$, —S(O)NR$^{b3}$R$^{c3}$, —S(O)$_2$R$^{a1}$, and —S(O)$_2$NR$^{b3}$R$^{c3}$;

each occurrence of R$^{b2}$, R$^{c2}$, and R$^{d2}$ is independently selected from the group consisting of: H and C$_{1-6}$ alkyl optionally substituted with from 1-2 R$^A$;

each occurrence of R$^{b3}$, R$^{c3}$, R$^{d3}$, and R$^{e2}$ is independently selected from the group consisting of: H; C$_{1-6}$ alkyl optionally substituted with from 1-2 R$^A$; —SO$_2$(C$_{1-6}$ alkyl), —C(O)(C$_{1-6}$ alkyl), and —C(O)O(C$_{1-6}$ alkyl);

each occurrence of R$^{G1A}$, R$^{G1B}$, R$^{G1A}$, R$^{G1B}$, R$^4$, R$^{4'}$, R$^5$, R$^6$, and R$^{6'}$ is independently selected from the group consisting of: H; R$^{a1}$; halo, —CN, —NO$_2$, —N$_3$, —OH, —OR$^{a1}$, —SH, —SR$^{a1}$, —C(O)H, —C(O)R$^{a1}$, —C(O) NR$^{b1}$R$^{c1}$, —C(O)OH, —C(O)OR$^{a1}$, —OC(O)H, —OC(O) R$^{a1}$, —OC(O)NR$^{b1}$R$^{c1}$, —C(=NR$^{e1}$)NR$^{b1}$R$^{c1}$, —NR$^{d1}$C (=NR$^{e1}$)NR$^{b1}$R$^{c1}$, —NR$^{b1}$R$^{c1}$, —$^+$NR$^{b2}$R$^{c2}$R$^{d2}$, —NR$^{d1}$C (O)H, —NR$^{d1}$C(O)R$^{a1}$, —NR$^{c1}$C(O)OR$^{a1}$, —NR$^{d1}$C(O) NR$^{b1}$R$^{c1}$, —NR$^{d1}$S(O)R$^{a1}$, —NR$^{d1}$S(O)$_2$R$^{a1}$, —NR$^{d1}$S(O)$_2$NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$;

each occurrence of R$^A$ is independently selected from the group consisting of: —CN; —OH; C$_{1-6}$ alkoxy; C$_{1-6}$ haloalkoxy; —C(O)NRR', wherein R' and R'' are each independently selected from H and C$_{1-4}$ alkyl; —C(O)OH; —C(O)O(C$_{1-6}$ alkyl); and —NR''R''', wherein R'' and R''' are each independently selected from the group consisting of H, C$_{1-4}$ alkyl, —SO$_2$(C$_{1-6}$ alkyl), —C(O)(C$_{1-6}$ alkyl), and —C(O)O(C$_{1-6}$ alkyl);

each occurrence of R$^B$ is independently selected from the group consisting of: halo; —CN; —OH; C$_{1-6}$ alkoxy; C$_{1-6}$ haloalkoxy; —C(O)NRR', wherein R' and R'' are each independently selected from H and C$_{1-4}$ alkyl; —C(O)OH; —C(O)O(C$_{1-6}$ alkyl); and —NR''R''', wherein R' and R''' are each independently selected from the group consisting of H, C$_{1-4}$ alkyl, —SO$_2$(C$_{1-6}$ alkyl), —C(O)(C$_{1-6}$ alkyl), and —C(O)O(C$_{1-6}$ alkyl);

each occurrence of R$^C$ is independently selected from the group consisting of: C$_{1-6}$ alkyl; C$_{1-4}$ haloalkyl; halo; —CN; —OH; oxo; C$_{1-6}$ alkoxy; C$_{1-6}$ haloalkoxy; —C(O)NRR', wherein R' and R''' are each independently selected from H and C$_{1-4}$ alkyl; —C(O)(C$_{1-6}$ alkyl); —C(O)OH; —C(O)O (C$_{1-6}$ alkyl); and —NR''R''', wherein R'' and R''' are each independently selected from the group consisting of H, C$_{1-4}$ alkyl, —SO$_2$(C$_{1-6}$ alkyl), —C(O)(C$_{1-6}$ alkyl), and —C(O)O (C$_{1-6}$ alkyl);

each occurrence of R$^D$ is independently selected from the group consisting of:
C$_{1-6}$ alkyl optionally substituted with from 1-2 substituents independently selected from the group consisting of: —OH, C$_{1-4}$ alkoxy; C$_{1-4}$ haloalkoxy; —NH$_2$, —NH (C$_{1-4}$ alkyl), and —N(C$_{1-4}$ alkyl)$_2$;

$C_{1-4}$ haloalkyl;
$C_{2-4}$ alkenyl;
$C_{2-4}$ alkynyl;
halo;
—CN;
—$NO_2$;
—$N_3$;
—OH;
$C_{1-6}$ alkoxy;
$C_{1-6}$ haloalkoxy;
—C(O)NRR', wherein R' and R" are each independently selected from H and $C_{1-4}$ alkyl;
$SO_2$NRR', wherein R' and R" are each independently selected from H and $C_{1-4}$ alkyl;
—C(O)($C_{1-6}$ alkyl);
—C(O)OH;
—C(O)O($C_{1-6}$ alkyl);
—$SO_2$($C_{1-6}$ alkyl);
—NR"R''', wherein R" and R''' are each independently selected from the group consisting of H, $C_{1-4}$ alkyl, —$SO_2$($C_{1-6}$ alkyl), —C(O)($C_{1-6}$ alkyl), and —C(O)O ($C_{1-6}$ alkyl);
($C_{3-10}$ cycloalkyl)-$(CH_2)_{0-2}$, wherein the $CH_2$ (when present) serves as the point of attachment, and wherein the $C_{3-10}$ cycloalkyl is optionally substituted with from 1-5 independently selected $C_{1-4}$ alkyl;
(heterocyclyl as defined above)-$(CH_2)_{0-2}$, wherein the $CH_2$ (when present) serves as the point of attachment, and wherein the heterocyclyl is optionally substituted with from 1-5 independently selected $C_{1-4}$ alkyl;
(phenyl)-$(CH_2)_{0-2}$, wherein the $CH_2$ (when present) serves as the point of attachment, and wherein the phenyl is optionally substituted with from 1-5 substituents independently selected from halo, $C_{1-4}$ alkyl, —$CF_3$, —$OCH_3$, —$SCH_3$, —$OCF_3$, —$NO_2$, —$N_3$, —$NH_2$, —NH($C_{1-4}$ alkyl), —N($C_{1-4}$ alkyl)$_2$, —C(O) ($C_{1-4}$ alkyl), —C(O)OH, —C(O)O($C_{1-4}$ alkyl), —$SO_2$ ($CH_3$), and cyclopropyl;
(heteroaryl as defined above)-$(CH_2)_{0-2}$, wherein the $CH_2$ (when present) serves as the point of attachment, and wherein the phenyl is optionally substituted with from 1-5 substituents independently selected from halo, $C_{1-4}$ alkyl, —$CF_3$, —$OCH_3$, —$SCH_3$, —$OCF_3$, —$NO_2$, —$N_3$, —$NH_2$, —NH($C_{1-4}$ alkyl), —N($C_{1-4}$ alkyl)$_2$, —C(O)($C_{1-4}$ alkyl), —C(O)OH, —C(O)O($C_{1-4}$ alkyl), —$SO_2$($CH_3$), and cyclopropyl; and In some embodiments, one, two, three, four, five, six, seven, or eight of the following apply:

(a) $X^1$ and $X^5$ cannot both be —OH;
(b) $X^1$ and $X^5$ cannot both be halo (e.g., $X^1$ and $X^5$ cannot both be —F); in certain embodiments, when A and B are each independently selected from formula (i) and formula (ii), then $X^1$ and $X^5$ cannot both be halo (e.g., $X^1$ and $X^5$ cannot both be —F);
(c) $X^1$ and $X^5$ cannot both be —$OR^{a1}$ when each occurrence of $R^{a1}$ is $C_{1-10}$ alkyl optionally substituted with from 1-3 $R^A$ (e.g., when each occurrence of $R^{a1}$ is $C_{1-4}$ alkyl optionally substituted with from 1-2 $R^A$; when each occurrence of $R^{a1}$ is $C_{1-4}$ alkyl; e.g., when each occurrence of $R^{a1}$ is methyl or ethyl);
(d) $X^1$ and $X^5$ cannot both be —$OR^{a1}$ when each occurrence of $R^{a1}$ is heterocyclyl, including from 3-10 ring atoms, wherein from 1-3 ring atoms are independently selected from the group consisting of nitrogen, oxygen and sulfur, and which is optionally substituted with from 1-5 $R^C$; (in certain of these embodiments, the heterocyclyl, includes from 5-7 ring atoms; e.g., 6 ring atoms, e.g., optionally substituted pyranyl or piperidinyl);
(e) $X^1$ and $X^5$ cannot both be —$OR^{a1}$ when each occurrence of $R^{a1}$ is when each occurrence of $R^{a1}$ is (heterocyclyl as defined above)-$C_{1-6}$ alkylene; in certain of these embodiments, the heterocyclyl, includes from 5-7 ring atoms; e.g., 6 ring atoms, e.g., optionally substituted pyranyl or piperidinyl);
(f) $X^1$ and $X^5$ cannot both be —OC(O)$R^{a1}$ when each occurrence of $R^{a1}$ is $C_{1-10}$ alkyl optionally substituted with from 1-3 $R^A$ (e.g., when each occurrence of $R^{a1}$ is $C_{1-4}$ alkyl optionally substituted with from 1-2 $R^A$; e.g., when each occurrence of $R^{a1}$ is $C_{1-4}$ alkyl; e.g., when each occurrence of $R^{a1}$ is methyl);
(g) $X^1$ and $X^5$ cannot both be —OC(O)$R^{a1}$ when each occurrence of $R^{a1}$ is $C_{6-10}$ aryl (e.g., phenyl) optionally substituted with from 1-5 $R^D$; and
(h) when one of $X^1$ and $X^5$ is —OH, then the other of $X^1$ and $X^5$ cannot be:
halo (e.g., —F);
OC(O)$NR^{b1}R^{c1}$;
OC(O)$R^{a1}$ (e.g., when each occurrence of $R^{a1}$ is $C_{6-10}$ aryl (e.g., phenyl) optionally substituted with from 1-5 $R^D$); or
—$OR^{a1}$ (e.g., when each occurrence of $R^{a1}$ is $C_{1-10}$ alkyl optionally substituted with from 1-3 $R^A$ (e.g., when each occurrence of $R^{a1}$ is $C_{1-4}$ alkyl optionally substituted with from 1-2 $R^A$; when each occurrence of $R^{a1}$ is $C_{1-4}$ alkyl; e.g., when each occurrence of $R^{a1}$ is methyl or ethyl).

Variables X, X', $G^1$, and $G^1$

In some embodiments, the compounds have formula (B). In some embodiments, the compounds have formula (I).

In some embodiments, X and X' are each O. In some embodiments, $G^1$ is a bond connecting (i) the carbon directly attached to $X^2$ and (ii) the carbon directly attached to $C(R^{2A})(R^{2B})(X^6)$. In some embodiments, $G^2$ is a bond connecting (i) the carbon directly attached to $X^4$ and (ii) the carbon directly attached to $C(R^{1A})(R^{1B})(X^3)$.

In some embodiments, X and X' are each O, $G^1$ is a bond connecting (i) the carbon directly attached to $X^2$ and (ii) the carbon directly attached to $C(R^{2A})(R^{2B})(X^6)$, $G^2$ is a bond connecting (i) the carbon directly attached to $X^4$ and (ii) the carbon directly attached to $C(R^{1A})(R^{1B})(X^3)$, and the compound has formula (A'), (B'), or (I-A) described previously.

Variables A and B

In some embodiments, A and B are each independently selected from the group consisting of formula (i) and formula (ii). In certain embodiments, A has formula (i), and B has formula (ii); or A has formula (ii), and B has formula (i). In other embodiments, A has formula (ii), and B has formula (ii). In still other embodiments, A has formula (i), and B has formula (i).

In some embodiments, each occurrence of $Z^1$ is N, and $Z^{1'}$ is N. In some embodiments, $R^5$ is —$NR^{b1}R^{c1}$ (e.g., —$NH_2$ or —$NHR^{c1}$). In some embodiments, each occurrence of $Z^1$ is N, $Z^{1'}$ is N, and $R^5$ is —$NR^{b1}R^{c1}$ (e.g., —$NH_2$ or —$NHR^{c1}$). In certain of these embodiments, $R^4$ and/or $R^6$ is H; or $R^4$ is other than H, and $R^6$ is H.

In some embodiments, each occurrence of $Z^1$ is N, and $Z^{1'}$ is N. In some embodiments, $R^5$ is —OH. In some embodiments, each occurrence of $Z^1$ is N, $Z^{1'}$ is N, and $R^5$ is —OH. In certain of these embodiments, $R^6$ is H. In certain of these embodiments, $R^4$ is H; in other embodiments, $R^4$ is other than H. For example, each occurrence of $Z^1$ is N; $Z^{1'}$ is N; $R^5$ is —OH; $R^6$ is H; and $R^4$ is H.

In some embodiments, each occurrence of $Z^2$ is N, $Z^{2'}$ is N, and $Z^3$ is N—$R^3$ (e.g., N—H). In some embodiments, $R^{6'}$ is —$NR^{b1}R^{c1}$ (e.g., —$NH_2$ or —$NHR^{c1}$). In some embodiments, each occurrence of $Z^2$ is N, $Z^{2'}$ is N, $Z^3$ is N—$R^3$ (e.g., N—H), and $R^{6'}$ is —$NR^{b1}R^{c1}$ (e.g., —$NH_2$ or —$NHR^{c1}$). In certain of these embodiments, $R^{4'}$ is H; in other embodiments, $R^{4'}$ is other than H.

Variables $X^2$, $X^3$, $X^4$ and $X^6$

In some embodiments, each of $X^2$, $X^3$, $X^4$ and $X^6$ is O.

Variables $X^1$ and $X^5$

In some embodiments, $X^1$ is —OH, —$OR^{a1}$, —F, —SH, —$SR^{a1}$, —OC(O)H, —OC(O)$R^{a1}$, —OC(O)$NR^{b1}R^{c1}$, —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$ or —$NR^{d1}S(O)_2NR^{b1}R^{c1}$ (in certain embodiment, $X^1$ is other than —F).

In certain embodiments, $X^1$ is —OH, —$OR^{a1}$, —OC(O)H, —OC(O)$R^{a1}$, —OC(O)$NR^{b1}R^{c1}$, —F, —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$ (in certain embodiment, $X^1$ is other than —F).

In certain embodiments, $X^1$ is —F, —OH, —$OR^{a1}$, —OC(O)H, —OC(O)$R^{a1}$, or —OC(O)$NR^{b1}R^{c1}$ (in certain embodiment, $X^1$ is other than —F).

In certain embodiments, $X^1$ is —F, —OH or —$OR^{a1}$ (in certain embodiment, $X^1$ is other than —F).

In certain embodiments, $X^1$ is —OH.

In other embodiments, $X^1$ is —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$; e.g., —$NR^{b1}R^{c1}$ or —$^+NR^{b1}R^{c1}R^{d1}$; e.g., —$NH_2$, —$^-NH_3$, or $NHR^{c1}$.

In other embodiments, $X^1$ is —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$; —$NR^{d1}C(O)H$; —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$; e.g., —$NR^{b1}R^{c1}$ or —$^+NR^{b1}R^{c1}R^{d1}$; e.g., —$NH_2$, —$^-NH_3$, or $NHR^{c1}$, each of $X^2$, $X^3$, $X^4$ and $X^6$ is O.

In some embodiments, the carbon directly attached to $X^1$ has the (R)-configuration.

In some embodiments, the carbon directly attached to $X^1$ has the (S)-configuration.

In some embodiments, $X^5$ is —OH, —$OR^{a1}$, —F, —SH, —$SR^{a1}$, —OC(O)H, —OC(O)$R^{a1}$, —OC(O)$NR^{b1}R^{c1}$, —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$ (in certain embodiment, $X^5$ is other than —F).

In certain embodiments, $X^5$ is —OH, —$OR^{a1}$, —OC(O)H, —OC(O)$R^{a1}$, —OC(O)$NR^{b1}R^{c1}$, —F, —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$ (in certain embodiment, $X^5$ is other than —F).

In certain embodiments, $X^5$ is —F, —OH, —$OR^{a1}$, —OC(O)H, —OC(O)$R^{a1}$, or —OC(O)$NR^{b1}R^{c1}$ (in certain embodiment, $X^5$ is other than —F).

In certain embodiments, $X^5$ is —F, —OH or —$OR^{a1}$ (in certain embodiment, $X^5$ is other than —F).

In certain embodiments, $X^5$ is —OH.

In other embodiments, $X^5$ is —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$; e.g., —$NR^{b1}R^{c1}$ or —$^+NR^{b1}R^{c1}R^{d1}$; e.g., —$NH_2$, —$^-NH_3$, or $NHR^{c1}$.

In other embodiments, $X^5$ is —$NO_2$, —$N_3$, —$NR^{d1}C(=NR^{e1})NR^{b1}R^{c1}$, —$NR^{b1}R_{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$; e.g., —$NR^{b1}R^{c1}$ or —$^+NR^{b1}R^{c1}R^{d1}$; e.g., —$NH_2$, —$^-NH_3$, $NHR^{c1}$, and each of $X^2$, $X^3$, $X^4$ and $X^6$ is O.

In some embodiments, the carbon directly attached to $X^5$ has the (R)-configuration.

In some embodiments, the carbon directly attached to $X^5$ has the (S)-configuration.

In some embodiments, $X^1$ and $X^5$ are each independently selected from —OH, —$OR^{a1}$, —F, —SH, —$SR^{a1}$, —OC(O)H, —OC(O)$R^{a1}$, —OC(O)$NR^{b1}R^{c1}$, —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$ (in certain embodiment, $X^1$ and/or $X^5$ is other than —F). $X^1$ and $X^5$ can be the same or different.

In certain embodiments, $X^1$ and $X^5$ are each independently selected from —OH, —$OR^{a1}$, —OC(O)H, —OC(O)$R^{a1}$, —OC(O)$NR^{b1}R^{c1}$, —F, —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$ (in certain embodiment, $X^5$ is other than —F).

In certain embodiments, $X^1$ and $X^5$ are each independently selected from —F, —OH, —$OR^{a1}$, —OC(O)H, —OC(O)$R^{a1}$, or —OC(O)$NR^{b1}R^{c1}$ (in certain embodiment, $X^5$ is other than —F).

In certain embodiments, $X^1$ and $X^5$ are each independently selected from —F, —OH or —$OR^{a1}$ (in certain embodiment, $X^5$ is other than —F).

In certain embodiments, $X^1$ and $X^5$ are each —OH.

In other embodiments, $X^1$ and $X^5$ are each independently selected from —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$; e.g., —$NR^{b1}R^{c1}$ or —$^+NR^{b1}R^{c1}R^{d1}$; e.g., —$NH_2$, —$^+NH_3$, or $NHR^{c1}$.

In other embodiments, $X^1$ and $X^5$ are each independently selected from —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$; e.g., —$NR^{b1}R^{c1}$ or —$^+NR^{b1}R^{c1}R^{d1}$; e.g., —$NH_2$, —$^-NH_3$, or $NHR^{c1}$, and each of $X^2$, $X^3$, $X^4$ and $X^6$ is O.

In some embodiments, one of $X^1$ and $X^5$ is other than —OH.

In some embodiments, one of $X^1$ and $X^5$ is other than halo.

In some embodiments, one of $X^1$ and $X^5$ is other than —F.

In some embodiments, one of $X^1$ and $X^5$ is other than —$OR^{a1}$. In certain of these embodiments, $R^{a1}$ is:

$C_{1-10}$ alkyl optionally substituted with from 1-3 $R^A$ (e.g., when each occurrence of $R^{a1}$ is $C_{1-4}$ alkyl optionally substituted with from 1-2 $R^A$; when each occurrence of $R^{a1}$ is $C_{1-4}$ alkyl; e.g., when each occurrence of $R^{a1}$ is methyl or ethyl); and/or heterocyclyl, including from 3-10 ring atoms, wherein from 1-3 ring atoms are independently selected from the group consisting of nitrogen, oxygen and sulfur, and which is optionally substituted with from 1-5 $R^C$; (in certain of these embodiments, the heterocyclyl, includes from 5-7 ring atoms; e.g., 6 ring atoms, e.g., $R^{a1}$ is optionally substituted pyranyl or piperidinyl); and/or (heterocyclyl as defined above)-$C_{1-6}$ alkylene; in certain of these embodiments, the heterocyclyl portion includes from 5-7 ring atoms; e.g., 6 ring atoms, e.g., optionally substituted pyranyl or piperidinyl).

In some embodiments, one of $X^1$ and $X^5$ is other than —OC(O)$R^{a1}$. In certain of these embodiments, $R^{a1}$ is:

$C_{1-10}$ alkyl optionally substituted with from 1-3 $R^A$ (e.g., when each occurrence of $R^{a1}$ is $C_{1-4}$ alkyl optionally substituted with from 1-2 $R^A$; when each occurrence of $R^{a1}$ is $C_{1-4}$ alkyl; e.g., when each occurrence of $R^{a1}$ is methyl; and/or $C_{6-10}$ aryl (e.g., phenyl) optionally substituted with from 1-5 $R^D$.

In some embodiments, one of $X^1$ and $X^5$ is other than —OC(O)NR$^{b1}$R$^{c1}$.

In some embodiments, one of $X^1$ and $X^5$ is other than —OH and halo. In certain embodiments, one of $X^1$ and $X^5$ is other than —OH and —F.

In some embodiments, one of $X^1$ and $X^5$ is other than —OH, halo (e.g., —F), —OR$^{a1}$, and —OC(O)R$^{a1}$.

In some embodiments, one of $X^1$ and $X^5$ is other than —OH, halo (e.g., —F), —OR$^{a1}$, —OC(O)R$^{a1}$, and —OC(O)NR$^{b1}$R$^{c1}$.

In some embodiments, one of $X^1$ and $X^5$ is selected from the group consisting of H, $C_{1-4}$ alkyl, $C_{1-4}$ haloalkyl, —CN, —NO$_2$, —N$_3$, —SH, —SR$^{a1}$, —C(O)H, —C(O)R$^{a1}$, —C(O)NR$^{b1}$R$^{c1}$, —C(O)OH, —C(O)OR$^{a1}$, —C(=NR$^{c1}$)NR$^{b1}$R$^{c1}$, —NR$^{d1}$C(=NR$^{e1}$)NR$^{b1}$R$^{c1}$, —NR$^{b1}$C$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, —NR$^{d1}$S(O)$_2$NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$; and the other is as defined anywhere herein.

In certain embodiments, one of $X^1$ and $X^5$ is selected from the group consisting of H, $C_{1-4}$ alkyl, $C_{1-4}$ haloalkyl, —CN, —NO$_2$, —N$_3$, —C(O)H, —C(O)R$^{a1}$, —C(O)NR$^{b1}$R$^{c1}$, —C(O)OH, —C(O)OR$^{a1}$, —C(=NR$^{e1}$)NR$^{b1}$R$^{c1}$, —NR$^{d1}$C(=NR$^{e1}$)NR$^{b1}$R$^{c1}$, —NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, —NR$^{d1}$S(O)$_2$NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$; and the other is as defined anywhere herein.

In certain embodiments, one of $X^1$ and $X^5$ is selected from the group consisting of H, $C_{1-4}$ alkyl, $C_{1-4}$ haloalkyl, —CN, —NO$_2$, —N$_3$, —C(O)R$^{a1}$, —C(O)NR$^{b1}$R$^{c1}$, —C(O)OH, —C(O)OR$^{a1}$, —C(=NR$^{c1}$)NR$^{b1}$R$^{c1}$, —NR$^{d1}$C(=NR$^{c1}$)NR$^{b1}$R$^{c1}$, —NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, and —NR$^{d1}$S(O)$_2$NR$^{b1}$R$^{c1}$; and the other is as defined anywhere herein.

In certain embodiments, one of $X^1$ and $X^5$ is selected from the group consisting of H, $C_{1-4}$ alkyl, $C_{1-4}$ haloalkyl, —CN, —NO$_2$, —N$_3$, —NR$^{d1}$C(=NR$^{e1}$)NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, and —NR$^{d1}$S(O)$_2$NR$^{b1}$R$^{c1}$; and the other is as defined anywhere herein.

In certain embodiments, one of $X^1$ and $X^5$ is selected from the group consisting of —NO$_2$, —N$_3$, —NR$^{d1}$C(=NR$^{e1}$)NR$^{b1}$R$^{c1}$, —NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, and —NR$^{d1}$S(O)$_2$NR$^{b1}$R$^{c1}$; and the other is as defined anywhere herein.

In certain embodiments, one of $X^1$ and $X^5$ is selected from the group consisting of —NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, and —NR$^{d1}$S(O)$_2$NR$^{b1}$R$^{c1}$; and the other is as defined anywhere herein.

In certain embodiments, one of $X^1$ and $X^5$ is selected from the group consisting of —NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, and —NR$^{d1}$C(O)NR$^{b1}$R$^{c1}$; and the other is as defined anywhere herein.

In certain embodiments, one of $X^1$ and $X^5$ is selected from the group consisting of —NR$^{b1}$R$^{c1}$ and —$^-$NR$^{b2}$R$^{c2}$R$^{d2}$; and the other is as defined anywhere herein.

In certain embodiments, one of $X^1$ and $X^5$ is selected from the group consisting —NH$_2$, —$^+$NH$_3$, and NHR$^{c1}$; and the other is as defined anywhere herein.

In some embodiments, each of $X^1$ and $X^5$ is independently selected from the group consisting of H, $C_{1-4}$ alkyl, $C_{1-4}$ haloalkyl, —CN, —NO$_2$, —N$_3$, —SH, —SR$^{a1}$, —C(O)H, —C(O)R$^{a1}$, —C(O)NR$^{b1}$R$^{c1}$, —C(O)OH, —C(O)OR$^{a1}$, —C(=NR$^{e1}$)NR$^{b1}$R$^{c1}$, —NR$^{d1}$C(=NR$^{e1}$)NR$^{b1}$R$^{c1}$, —NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, —NR$^{d1}$S(O)$_2$NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$.

In certain embodiments, each of $X^1$ and $X^5$ is independently selected from the group consisting of H, $C_{1-4}$ alkyl, $C_{1-4}$ haloalkyl, —CN, —NO$_2$, —N$_3$, —C(O)H, —C(O)R$^{a1}$, —C(O)NR$^{b1}$R$^{c1}$, —C(O)OH, —C(O)OR$^{a1}$, —C(=NR$^{e1}$)NR$^{b1}$R$^{c1}$, —NR$^{d1}$C(=NR$^{e1}$)NR$^{b1}$R$^{c1}$, —NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, —NR$^{d1}$S(O)$_2$NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$.

In certain embodiments, each of $X^1$ and $X^5$ is independently selected from the group consisting of H, $C_{1-4}$ alkyl, $C_{1-4}$ haloalkyl, —CN, —NO$_2$, N$^{d3}$, —C(O)H, —C(O)R$^{a1}$, —C(O)NR$^{b1}$R$^{c1}$, —C(O)OH, —C(O)OR$^{a1}$, —C(=NR$^{e1}$)NR$^{b1}$R$^{c1}$, —NR$^{d1}$C(=NR$^{e1}$)NR$^{b1}$R$^{c1}$, —NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, and —NR$^{d1}$S(O)$_2$NR$^{b1}$R$^{c1}$.

In certain embodiments, each of $X^1$ and $X^5$ is independently selected from the group consisting of H, $C_{1-4}$ alkyl, $C_{1-4}$ haloalkyl, —CN, —NO$_2$, —N$_3$, —NR$^{d1}$C(=NR$^{e1}$)NR$^{b1}$R$^{a1}$, —NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, and —NR$^{d1}$S(O)$_2$NR$^{b1}$R$^{c1}$.

In certain embodiments, each of $X^1$ and $X^5$ is independently selected from the group consisting of —NO$_2$, —N$_3$, —NR$^{d1}$C(=NR$^{e1}$)NR$^{b1}$R$^{c1}$, —NR$^{b1}$R$^{c1}$, —NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, and —NR$^{d1}$S(O)$_2$NR$^{b1}$R$^{c1}$.

In certain embodiments, each of $X^1$ and $X^5$ is independently selected from the group consisting of —NR$^{b1}$R$^{c1}$, —$^+$NR$^{b2}$R$^{c2}$R$^{d2}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, and —NR$^{d1}$S(O)$_2$NR$^{b1}$R$^{c1}$.

In certain embodiments, each of $X^1$ and $X^5$ is independently selected from the group consisting of —$NR^{b1}R^{c1}$, —$^+NR^{b2}R^{c2}R^{d2}$, —$NR^{d1}C(O)H$, —$NR^{d1}C(O)R^{a1}$, —$NR^{d1}C(O)OR^{a1}$, and —$NR^{d1}C(O)NR^{b1}R^{c1}$.

In certain embodiments, each of $X^1$ and $X^5$ is independently selected from the group consisting of —$NR^{b1}R^{c1}$ and —$^+NR^{b2}R^{c2}R^{d2}$.

In certain embodiments, each of $X^1$ and $X^5$ is independently selected from the group consisting —$NH_2$, —$^+NH_3$, and $NHR^{c1}$.

In some embodiments, the carbon directly attached to $X^1$ and the carbon directly attached to $X^5$ both have the (R)-configuration.

In some embodiments, the carbon directly attached to $X^1$ and the carbon directly attached to $X^5$ both have the (S)-configuration.

In some embodiments, the carbon directly attached to $X^1$ and the carbon directly attached to $X^5$ have opposite configurations (i.e., one has the (R)-configuration, and the other has the (S-configuration).

Variables $L^1$ and $L^2$

In some embodiments, $L^1$ is

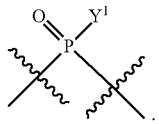

In some embodiments, $Y^1$ is —OH, —$OR^{a1}$, $O^-$, —SH, —$SR^{a1}$, or S. In certain embodiments, $Y^1$ is —OH, —$OR^{a1}$, or $O^-$ (e.g., —$OR^{a1}$ or $O^-$). In other embodiments, $Y^1$ is —SH or $S^-$. In certain of these embodiments, $L^1$ has the $R_P$ configuration, or $L^1$ has the $S_P$ configuration.

In some embodiments, $L^2$ is

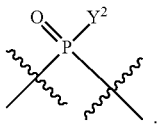

In some embodiments, $Y^2$ is —OH, —$OR^{a1}$, $O^-$, —SH, —$SR^{a1}$, or S. In certain embodiments, $Y^2$ is —OH, —$OR^{a1}$, or $O^-$ (e.g., —$OR^{a1}$ or $O^-$). In other embodiments, $Y^2$ is —SH or $S^-$. In certain of these embodiments, $L^2$ has the $R_P$ configuration, or $L^2$ has the $S_P$ configuration.

In some embodiments, $L^1$ is

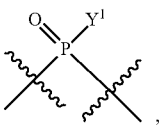

and $L^2$ is

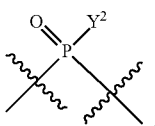

$Y^1$ and $Y^2$ can be the same or different. In some embodiments, $Y^1$ and $Y^2$ are each independently selected from is —OH, —$OR^{a1}$, $O^-$, —SH, —$SR^{a1}$, or S; e.g., —$OR^{a1}$ or $O^-$; e.g., —SH or $S^-$; e.g., $S^-$.

In certain embodiments, $Y^1$ and $Y^2$ are each $O^-$.

In certain embodiments, $Y^1$ and $Y^2$ are each —SH or $S^-$. In certain of these embodiments, $L^1$ and $L^2$ both have the $R_P$ configuration or both have the $S_P$ configuration. In other of these embodiments, one of $L^1$ and $L^2$ has the $R_P$ configuration, and the other has the $S_P$ configuration.

Variables $R^{1A}$ and $R^{1B}$ and $R^{2A}$ and $R^{2B}$

In some embodiments, $R^{1A}$ and $R^{1B}$ are each H. In some embodiments, $R^{2A}$ and $R^{2B}$ are each H. In some embodiments, $R^{1A}$ and $R^{1B}$ are each H, and $R^{2A}$ and $R^{2B}$ are each H.

Non-Limiting Combinations

In some embodiments of formula (A), (B), (I), (A'), (B'), or (I-A):

$X^1$ and $X^5$ are each independently selected from the group consisting of —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)R^{a1}$, —$NR^{d1}S(O)_2R^{a1}$, and —$NR^{d1}S(O)_2NR^{b1}R^{c1}$;

each of $X^2$, $X^3$, $X^4$ and $X^6$ is O;

$L^1$ is

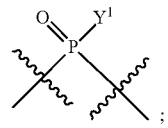

$L^2$ is

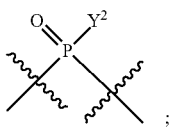

$Y^1$ and $Y^2$ are each independently selected from —OH, —$OR^{a1}$, $O^-$, —SH, —$SR^{a1}$, or S; and A and B are each independently selected from the group consisting of: formula (i) and formula (ii).

In some embodiments of formula (A), (B), (I), (A'), (B'), or (I-A):

$X^1$ and $X^5$ are each independently selected from the group consisting of —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, and —$NR^{d1}S(O)_2NR^{b1}R^{c1}$;

each of $X^2$, $X^3$, $X^4$ and $X^6$ is O;

$L^1$ is

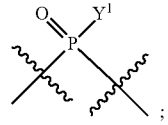

$L^2$ is

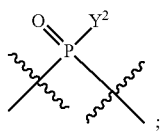

$Y^1$ and $Y^2$ are each independently selected from —OH, —$OR^{a1}$, $O^-$, —SH, —$SR^{a1}$, or S; and A and B are each independently selected from the group consisting of: formula (i) and formula (ii);

and optionally:

each occurrence of V is N, $Z^{1'}$ is N, and $R^5$ is —$NR^{b1}R^{c1}$ (e.g., —$NH_2$ or —$NHR^{c1}$); and in certain of these embodiments, $R^4$ and/or $R^6$ is H; or $R^4$ is other than H, and $R^6$ is H; and/or each occurrence of $Z^1$ is N, $Z^{1'}$ is N, and $R^5$ is —OH; in certain of these embodiments, $R^6$ is H; in certain of these embodiments, $R^4$ is H; in other embodiments, $R^4$ is other than H; and/or each occurrence of $Z^2$ is N, $Z^{2'}$ is. N, $Z^3$ is N—$R^3$ (e.g., N—H), and $R^{6'}$ is —$NR^{b1}R^{c1}$ (e.g., —$NH_2$ or —$NHR^{c1}$); and in certain of these embodiments, $R^{4'}$ is H; in other embodiments, $R^{4'}$ is other than H.

In some embodiments, the compound has formula (II):

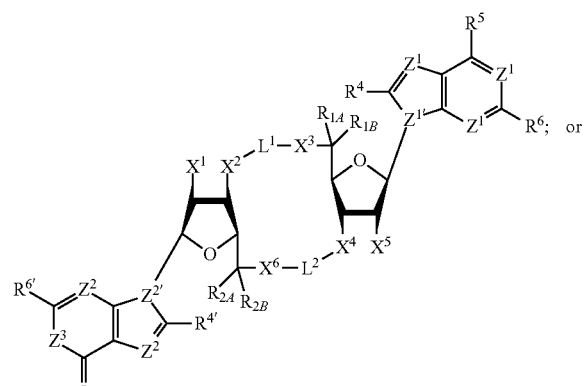

formula (II-A)

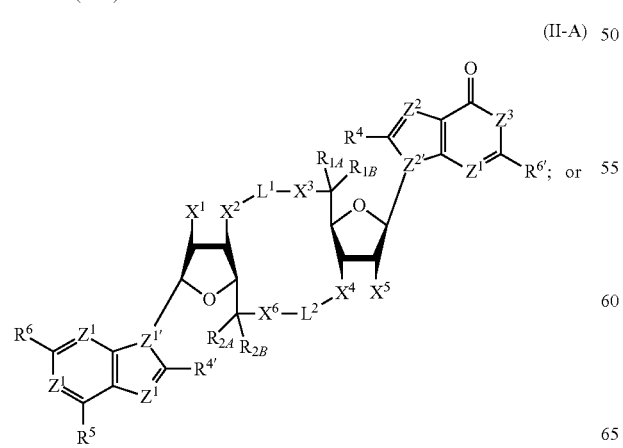

formula (III):

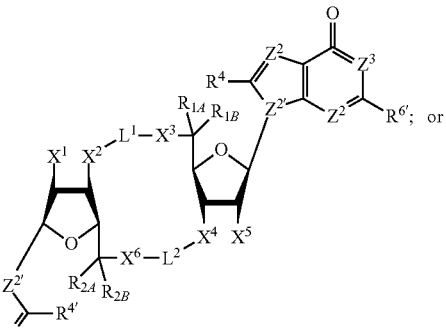

formula (IV):

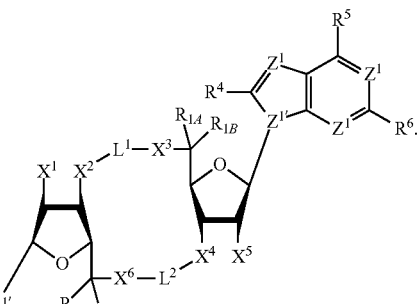

In some embodiments, the compound has formula (V):

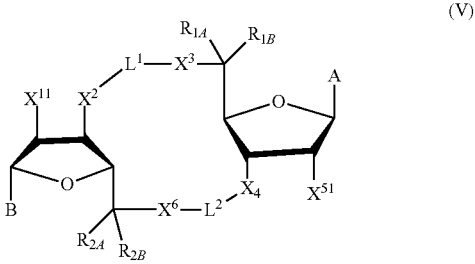

in which, $X^{11}$ and $X^{51}$ are each independently selected from the group consisting of —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, and —$NR^{d1}S(O)_2NR^{b1}R^{c1}$;

each of $X^2$, $X^3$, $X^1$ and $X^6$ is O;

$L^1$ is
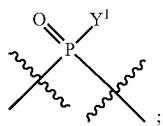
;
$L^2$ is
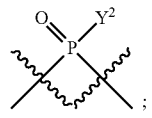
;
$Y^1$ and $Y^2$ are each independently selected from —OH, —OR$^{a1}$, O$^-$, —SH, —SR$^{a1}$, or S; and
A and B are each independently selected from the group consisting of: formula (i) and formula (ii).
Representative and non-limiting examples of formula I compounds are provided in Table 1.

TABLE 1-continued

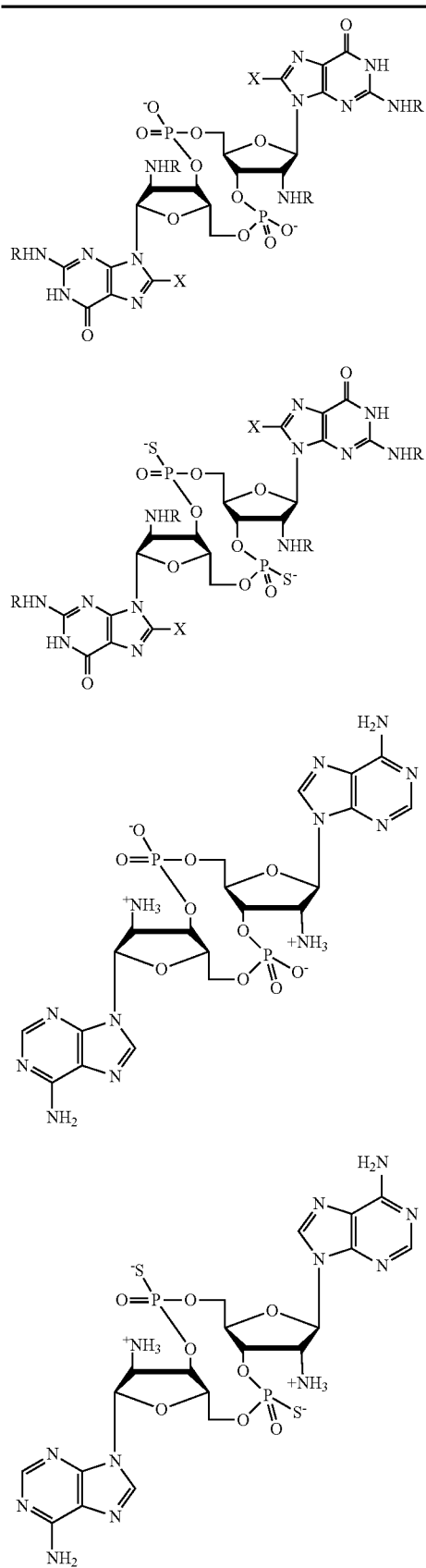

TABLE 1-continued

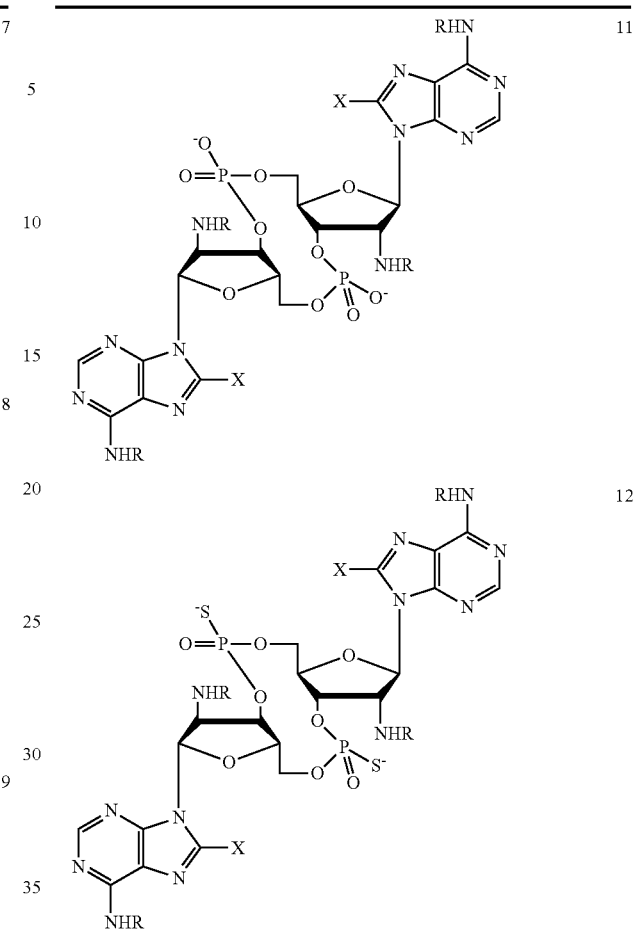

Pharmaceutical Compositions and Administration

General

In some embodiments, a chemical entity (e.g., a compound that modulates (e.g., agonizes or partially agonizes) STING, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-γ-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22$^{nd}$ Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intraburnal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "Effect of Intratumoral Injection on the Biodistribution and the Therapeutic Potential of HPMA Copolymer-Based Drug Delivery Systems" Neoplasia. 2006, 10, 788-795.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carb op ol, m ethyl oxyb enzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acidmethyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which a decrease or increase in STING activity (e.g., a decrease, e.g., repressed or impaired STING signaling) contributes to the pathology and/or symptoms and/or progression of the condition, disease or disorder (e.g., immune disorders, cancer) are provided. In certain embodiments, the chemical entities described herein induce an immune response in a subject (e.g., a human). In certain embodiments, the chemical entities described herein induce STING-dependent type I interferon production in a subject (e.g., a human).

Indications

In some embodiments, the condition, disease or disorder is cancer. Non-limiting examples of cancer include melanoma, carcinoma, lymphoma, blastoma, sarcoma, and leukemia or lymphoid malignancies. More particular examples of such cancers include breast cancer, colon cancer, rectal cancer, colorectal cancer, kidney or renal cancer, clear cell cancer lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, prostatic neoplasms, liver cancer, bladder cancer, cancer of the peritoneum, hepatocellular cancer, gastric or stomach cancer including gastrointestinal cancer, gastrointestinal stromal tumor, pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma, myelodysplasia disorders, myeloproliferative disorders, chronic myelogenous leukemia, and acute hematologic malignancies, endometrial or uterine carcinoma, endometriosis, endometrial stromal sarcoma, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, mast cell sarcoma, ovarian sarcoma, uterine sarcoma, melanoma, malignant mesothelioma, skin carcinomas, Schwannoma, oligodendroglioma, neuroblastomas, neuroectodermal tumor, rhabdomyosarcoma, osteogenic sarcoma, leiomyosarcomas, Ewing Sarcoma, peripheral primitive neuroectodermal tumor, urinary tract carcinomas, thyroid carcinomas, Wilm's tumor, as well as abnormal vascular proliferation associated with phakomatoses, edema (such as that associated with brain tumors), and Meigs' syndrome. In some cases, the cancer is melanoma.

In some embodiments, the condition, disease or disorder is a neurological disorder, which includes disorders that involve the central nervous system (brain, brainstem and cerebellum), the peripheral nervous system (including cranial nerves), and the autonomic nervous system (parts of which are located in both central and peripheral nervous system). Non-limiting examples of cancer include acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chi ari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme diseaseneurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjögren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

In some embodiments, the condition, disease or disorder is an autoimmune diseases. Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, modulation of the immune system by STING provides for the treatment of diseases, including diseases caused by foreign agents. Exemplary infections by foreign agents which may be treated and/or prevented by the method of the present invention include an infection by a bacterium (e.g., a Gram-positive or Gram-negative bacterium), an infection by a fungus, an infection by a parasite, and an infection by a virus. In one embodiment of the present invention, the infection is a bacterial infection (e.g., infection by *E. coli, Klebsiella pneumoniae, Pseudomonas aeruginosa, Salmonella* spp., *Staphylococcus aureus, Streptococcus* spp., or vancomycin-resistant enterococcus). In another embodiment, the infection is a fungal infection (e.g. infection by a mould, a yeast, or a higher fungus). In still another embodiment, the infection is a parasitic infection (e.g., infection by a single-celled or multicellular parasite, including *Giardia duodenalis, Cryptosporidium parvum, Cyclospora cayetanensis*, and *Toxoplasma gondiz*). In yet another embodiment, the infection is a viral infection (e.g., infection by a virus associated with AIDS, avian flu, chickenpox, cold sores, common cold, gastroenteritis, glandular fever, influenza, measles, mumps, pharyngitis, pneumonia, rubella, SARS, and lower or upper respiratory tract infection (e.g., respiratory syncytial virus)).

In some embodiments, the condition, disease or disorder is hepatits B (see, e.g., WO 2015/061294).

In some embodiments, the condition, disease or disorder is mucositis, also known as stomatitits, which can occur as a result of chemotherapy or radiation therapy, either alone or in combination as well as damage caused by exposure to radiation outside of the context of radiation therapy.

In some embodiments, the condition, disease or disorder is uveitis, which is inflammation of the uvea (e.g., anterior uveitis, e.g., iridocyclitis or iritis; intermediate uveitis (also known as pars planitis); posterior uveitis; or chorioretinitis, e.g., pan-uveitis).

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional chemotherapeutic agent is an immunomodulatory moiety, e.g., an immune checkpoint inhibitor. In certain of these embodiments, the immune checkpoint inhibitor targets an immune checkpoint receptor selected from the group consisting of CTLA-4, PD-1, PD-L1, PD-1 PD-L1, PD-1 PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, $TIM_3$, Phosphatidylserine-$TIM_3$, SIRPA-CD47, VEGF, Neuropilin, CD160, CD30, and CD155; e.g., CTLA-4 or PD1 or PD-L1). See, e.g., Postow, M. *J. Clin. Oncol.* 2015, 33, 1.

In certain of these embodiments, the immune checkpoint inhibitor is selected from the group consisting of: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, Bevacizumab, and 1VINRP1685A, and MGA271.

In certain embodiments, the additional chemotherapeutic agent is a STING agonist. For example, the STING agonist can comprise a flavonoid. Suitable flavonoids include, but are not limited to, 10-(carboxymethyl)-9(10H)acridone (CMA), 5,6-Dimethylxanthenone-4-acetic acid (DMXAA), methoxyvone, 6,4'-dimethoxyflavone, 4'-methoxyflavone, 3',6'-dihydroxyflavone, 7,2'-dihydroxyflavone, daidzein, formononetin, retusin 7-methyl ether, xanthone, or any combination thereof. In some aspects, the STING agonist can be 10-(carboxymethyl)-9(10H)acridone (CMA). In some aspects, the STING agonist can be 5,6-Dimethylxanthenone-4-acetic acid (DMXAA). In some aspects, the STING agonist can be methoxyvone. In some aspects, the STING agonist can be 6,4'-dimethoxyflavone. In some aspects, the STING agonist can be 4'-methoxyflavone. In some aspects, the STING agonist can be 3',6'-dihydroxyflavone. In some aspects, the STING agonist can be 7,2'-dihydroxyflavone. In some aspects, the STING agonist can be daidzein. In some aspects, the STING agonist can be formononetin. In some aspects, the STING agonist can be retusin 7-methyl ether. In some aspects, the STING agonist can be xanthone. In some aspects, the STING agonist can be any combination of the above flavonoids. Thus, for example, in some embodiments the flavonoid comprises DMXAA.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semisynthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an antimetabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a vinca alkaloid, a podophyllotoxin and/or a taxane. Vinca alkaloids, in general, bind to specific sites on tubulin, inhibiting the assembly of tubulin into microtubules, generally during the M phase of the cell cycle. In an embodiment, a vinca alkaloid is derived, without limitation, from the Madagascar periwinkle, *Catharanthus roseus* (formerly known as *Vinca rosea*). In an embodiment, a vinca alkaloid includes, without limitation, Vincristine, Vinblastine, Vinorelbine and/or Vindesine. In an embodiment, a taxane includes, but is not limited to, Taxol, Paclitaxel and/or Docetaxel. In a further embodiment a plant alkaloid or terpernoid is a synthetic, semisynthetic or derivative. In a further embodiment, a podophyllotoxin is, without limitation, an etoposide and/or teniposide. In an embodiment, a taxane is, without limitation, docetaxel and/or ortataxel. [021] In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocorti sol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, docetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613, which is incorporated herein by reference in its entirety.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the STING protein can serve as a biomarker for certain types of cancer, e.g., colon cancer and prostate cancer. In other embodiments, identifying a subject can include assaying the patient's tumor microenvironment for the absence of T-cells and/or presence of exhausted T-cells, e.g., patients having one or more cold tumors. Such patients can include those that are resistant to treatment with checkpoint inhibitors. In certain embodiments, such patients can be treated with a chemical entity herein, e.g., to recruit T-cells into the tumor, and in some cases, further treated with one or more checkpoint inhibitors, e.g., once the T-cells become exhausted.

In some embodiments, the chemical entities, methods, and compositions described herein can be administered to certain treatment-resistant patient populations (e.g., patients resistant to checkpoint inhibitors; e.g., patients having one or more cold tumors, e.g., tumors lacking T-cells or exhausted T-cells).

Compound Preparation and Biological Assays

As can be appreciated by the skilled artisan, methods of synthesizing the compounds of the formulae herein will be evident to those of ordinary skill in the art. For example, the compounds described herein can be synthesized using methods described in, e.g., US 2015/0056224, the contents of each of which are hereby incorporated by reference in their entirety. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and R G M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. Compounds can be assayed using the procedures described in, e.g., WO 2015/077354.

A number of embodiments of the invention have been described. Nevertheless, it will be understood that various modifications may be made without departing from the spirit and scope of the invention. Accordingly, other embodiments are within the scope of the following claims.

What is claimed is:

1. A compound which is

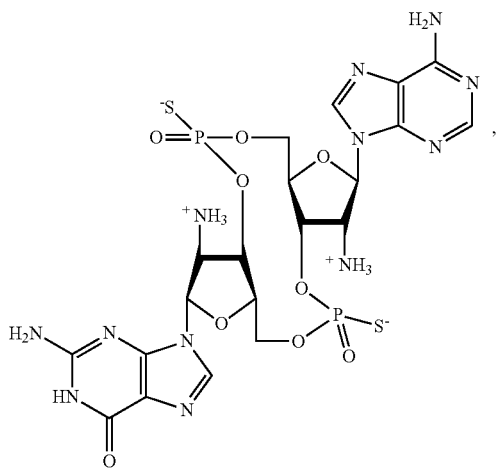

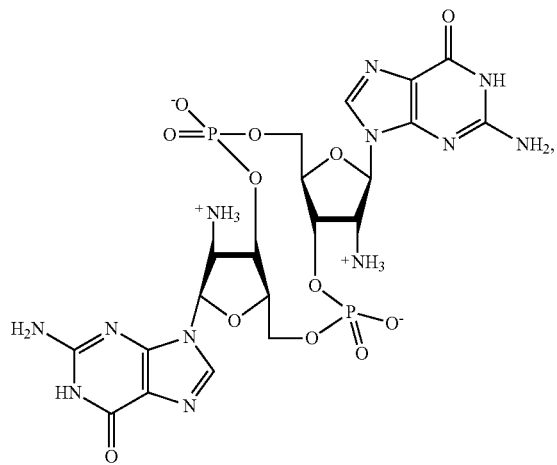

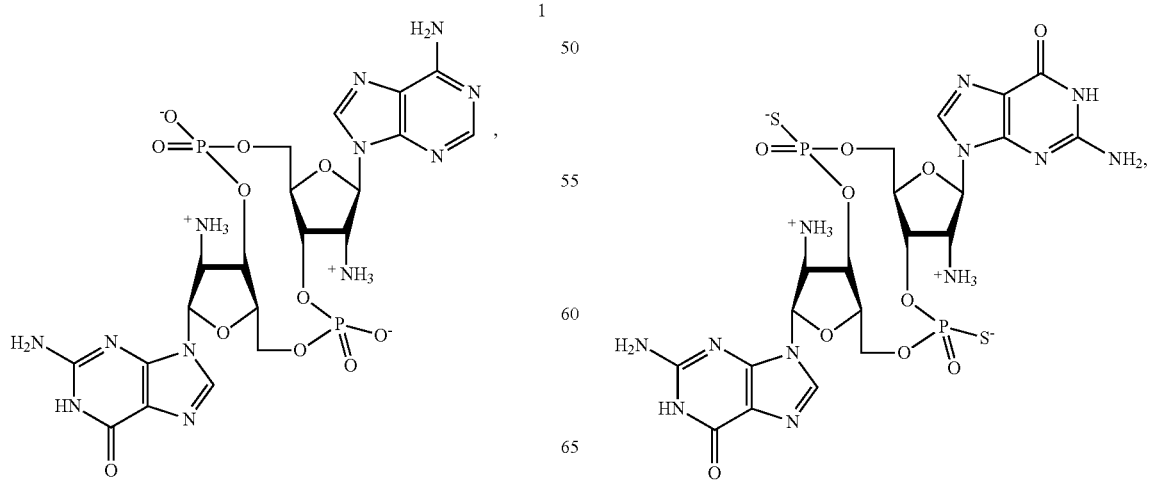

-continued
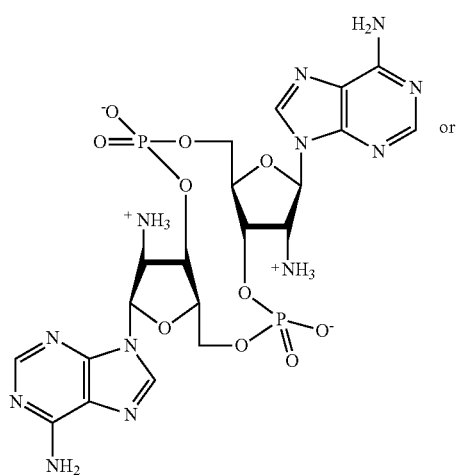
9
or
-continued
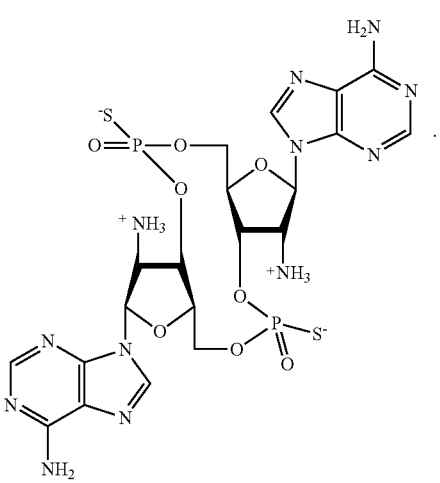
10
2. A pharmaceutical composition comprising a compound according to claim 1 or a pharmaceutically acceptable salt thereof and one or more pharmaceutically acceptable carriers, diluents or excipients.
* * * * *